United States Patent
Mori et al.

(10) Patent No.: US 7,252,939 B2
(45) Date of Patent: Aug. 7, 2007

(54) METHOD FOR SEPARATING AND PURIFYING A NUCLEIC ACID

(75) Inventors: Toshihiro Mori, Asaka (JP); Yoshihiko Makino, Asaka (JP)

(73) Assignee: Fujifilm Corporation, Toyko (JP)

( * ) Notice: Subject to any disclaimer, the term of this patent is extended or adjusted under 35 U.S.C. 154(b) by 518 days.

(21) Appl. No.: 10/621,412

(22) Filed: Jul. 18, 2003

(65) Prior Publication Data

US 2004/0058370 A1     Mar. 25, 2004

(30) Foreign Application Priority Data

Jul. 19, 2002     (JP)     ............... 2002-210833

(51) Int. Cl.
- *C12Q 1/68* (2006.01)
- *G01N 33/53* (2006.01)
- *G01N 33/567* (2006.01)
- *C07H 21/02* (2006.01)

(52) U.S. Cl. ............... 435/6; 435/7.1; 435/7.2; 536/23.1

(58) Field of Classification Search ............... 435/6, 435/7.1, 7.2; 536/23.1
See application file for complete search history.

(56) References Cited

FOREIGN PATENT DOCUMENTS

| EP | 1 316 606 A1 | 6/2003 |
|----|---|---|
| WO | WO 97/08547 A1 | 3/1997 |
| WO | WO 99/51316 A1 | 10/1999 |
| WO | WO 01/62976 A1 | 8/2001 |
| WO | WO 02/066993 A1 | 8/2002 |
| WO | WO 03/033739 A1 | 4/2003 |
| WO | WO 03/040687 A2 | 5/2003 |

OTHER PUBLICATIONS

Xing Su et al., Analytical Biochemistry, vol. 267, No. 2, Feb. 15, 1999, pp. 415-418.

Yun-ping Zhang et al.; Journal of Virological Methods, vol. 71, No. 1, 1998, pp. 45-50.

*Primary Examiner*—Jezia Riley
(74) *Attorney, Agent, or Firm*—Birch, Stewart, Kolasch & Birch, LLP

(57) ABSTRACT

An object of the present invention is to provide a method for separating and purifying a nucleic acid by adsorbing the nucleic acid in a test sample to a surface of a solid phase and desorbing the nucleic acid by washing and the like. The present invention provides a method for separating and purifying RNA from a nucleic acid mixture, comprising a step of: adsorbing and desorbing a nucleic acid in the nucleic acid mixture containing RNA and DNA to and from a solid phase of an organic macromolecule.

15 Claims, 3 Drawing Sheets

C = original miture
1 = comparative example
2 = present invention

METHOD FOR SEPARATING AND PURIFYING A NUCLEIC ACID

TECHNICAL FIELD

The present invention relates to a method of separating and purifying a nucleic acid. More specifically, the present invention relates to a method of separating and purifying RNA from a nucleic acid mixture containing RNA and DNA.

BACKGROUND ART

The nucleic acid is used in various fields in various forms. For example, in the field of recombinant nucleic acid technology, the nucleic acid is required to be used in the form of a probe, a genomic nucleic acid, and a plasmid nucleic acid.

In diagnostic field, the nucleic acid is also used in various methods, For example, a nucleic acid probe is normally used in detection and diagnosis of a human pathogen. Similarly, the nucleic acid is used in detection of genetic disorders. The nucleic acid is also used in detection of a food contamination substance. In addition, the nucleic acid is normally used in positioning, identification and isolation of an interesting nucleic acid by various reasons such as preparation of a gene map, cloning and expression of recombinant.

In many cases, the nucleic acid can be obtained in a very small amount, and a complicated and time-consuming operation is required for isolation and purification. This frequently time-consuming and complicated operation is easy to cause a loss of the nucleic acid. In purification of the nucleic acid obtained from serum, urine and bacterial culture, risks such as occurrence of contamination and pseudopositive result are added.

One of well known purification methods is exemplified by purification by adsorption of the nucleic acid to the surface of silicon dioxide, silica polymer or magnesium silicate followed by operations such as washing and desorbing (Japanese Examined Patent Application Publication No. 1995-51065.) This method is excellent in separation performance, however, there are problems that (1) it is difficult to industrially produce the adsorption medium of a comparable performance in a large scale, (2) the handling of the medium is inconvenient, and (3) it is difficult to process the medium in various shapes.

SUMMARY OF THE INVENTION

An object of the present invention is to provide a method for separating and purifying a nucleic acid by adsorbing the nucleic acid in a test sample to a surface of a solid phase and desorbing the nucleic acid by washing and the like. Another object of the present invention is to provide a method for separating and purifying the nucleic acid by using a solid phase which is excellent in separation performance and washing efficiency, can be easily processed, and can be mass-produced for those having substantially the same separation performance. A further object of the present invention is to provide a method for separating and purifying DNA from a nucleic acid mixture containing RNA and DNA.

The present inventors intensively studied to solve the above described objects. As a result, they have found that, in a method for separating and purifying a nucleic acid comprising steps of adsorbing and desorbing the nucleic acid to and from a solid phase, RNA can be separated from the nucleic acid mixture containing RNA and DNA by using an organic macromolecule as the solid phase and also using an unit for separation and purification of nucleic acid which contains the solid phase in a container having two openings. The invention has been completed on the basis of these findings.

According to the present invention, there is provided a method for separating and purifying RNA from a nucleic acid mixture, comprising a step of:

adsorbing and desorbing a nucleic acid in the nucleic acid mixture containing RNA and DNA to and from a solid phase of an organic macromolecule.

Preferably, the organic macromolecule is acetylcellulose, and more preferably triacetylcellulose.

Preferably, the organic macromolecule is an acetylcellulose having a surface-saponification rate of 0 to 50%, and more preferably an acetylcellulose having a surface-saponification rate of 0 to 20%.

Preferably, acetylcellulose is a porous film or a non-porous film.

Preferably, acetylcellulose is coated on beads.

Preferably in the method according to the present invention, the nucleic acid in a sample solution is adsorbed to and desorbed from the solid phase of organic macromolecule.

Preferably, the sample solution is a solution prepared by adding a water-soluble organic solvent to a solution obtained by treating a cell- or virus-containing test sample with a nucleic acid-solubilizing reagent.

Preferably, the nucleic acid-solubilizing reagent is a guanidine salt, a surfactant and a proteolytic enzyme.

Preferably, the method according to the present invention comprises steps of:

adsorbing the nucleic acid to the solid phase of the organic macromolecule;

washing the solid phase using a nucleic acid-washing buffer; and desorbing the nucleic acid adsorbed to the solid phase by using a liquid capable of desorbing the nucleic acid adsorbed to the solid phase.

Preferably, the nucleic acid-washing buffer is a solution containing 20 to 100% by weight of methanol, ethanol, isopropanol or n-propanol.

Preferably, the liquid capable of desorbing the nucleic acid adsorbed to the solid phase in a solution having a salt concentration of 0.5 M or lower.

Preferably, adsorption and desorption of the nucleic acid is carried out by using an unit for separation and purification of nucleic acid in which a container having at least two openings contains the solid phase of the organic macromolecule.

More preferably, adsorption and desorption of the nucleic acid is carried out by using an unit for separation and purification of nucleic acid which comprises (a) a solid phase of the organic macromolecule, (b) a container having at least two openings and containing the solid phase, and (c) a pressure difference-generating apparatus connected to one opening of the container.

Preferably, the method according to the present invention may be carried out by the following steps of:

(a) preparing a sample solution containing a nucleic acid by using a test sample and inserting one opening of an unit for separation and purification of nucleic acid into said sample solution containing the nucleic acid;

(b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase of the organic macromolecule;

(c) making the inside of the container in a pressurized condition by using the pressure difference-generating apparatus connected to the other opening of the unit for separation and purification of nucleic acid, and discharging the sample solution containing the sucked nucleic acid to an outside of the container;

(d) inserting one opening of the unit for separation and purification of nucleic acid into the nucleic acid-washing buffer;

(e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase of the organic macromolecule;

(f) making the inside of the container in the pressurized condition by using the pressure difference-generating apparatus connected to the other opening of the unit for separation and purification of nucleic acid, and discharging the sucked nucleic acid-washing buffer to the outside of the container;

(g) inserting one opening of the unit for separation and purification of nucleic acid into the liquid capable of desorbing the nucleic acid adsorbed to the solid phase of the organic macromolecule;

(h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule to contact the liquid to the solid phase; and (i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule to the outside of the container.

Alternatively, the method according to the present invention may be carried out by steps of:

(a) preparing a sample solution containing the nucleic acid using a test sample and injecting said sample solution containing the nucleic acid into one opening of the unit for separation and purification of nucleic acid;

(b) making the inside of the container in the pressurized condition by using the pressure difference-generating apparatus connected to said one opening of the unit for separation and purification of nucleic acid, and discharging the injected sample solution containing the nucleic acid from the other opening to contact the sample solution to the solid phase of the organic macromolecule;

(c) injecting the nucleic acid-washing buffer into said one opening of the unit for separation and purification of nucleic acid;

(d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule;

(e) injecting the liquid capable of desorbing the nucleic acid adsorbed to the solid phase of the organic macromolecule into said one opening of the unit for separation and purification of nucleic acid; and (f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule and discharge the nucleic acid to the outside of the container.

BRIEF DESCRIPTION OF THE DRAWINGS

In FIG. 2, 1 denotes a container, 10 denotes a main body, 101 denotes an opening, 102 denotes a bottom face, 103 denotes a frame, 104 denotes a wall, 105 denotes a step, 121 denotes a space, 122 denotes a space, 123 denotes a space, 13 denotes a pressing member, 131 denotes a hole, 132 denotes a projection, 20 denotes a lid, 21 denotes an opening, and 30 denotes a solid phase;

DETAILED DESCRIPTION OF THE INVENTION

Figure 1:
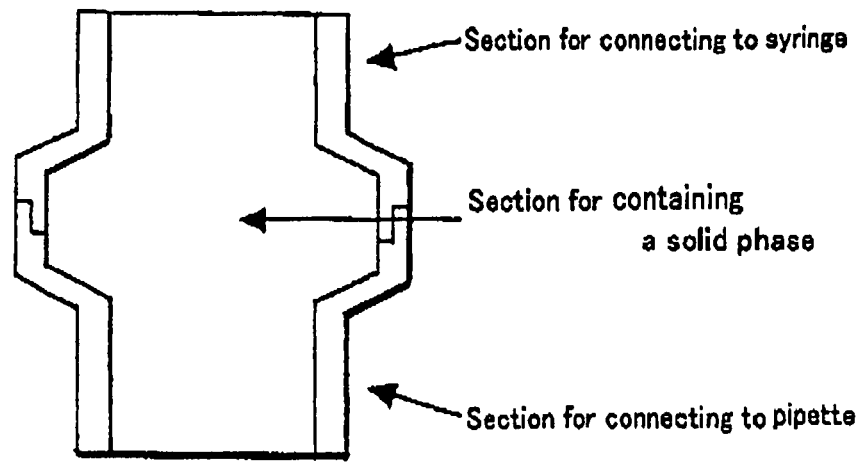
FIG. 1 shows a conceptual diagram of a unit for separation and purification of nucleic acid according to the present invention.

Embodiments of the present invention will be explained below.

The method for separating and purifying a nucleic acid according to the present invention relates to a method of separating and purifying RNA from a nucleic acid mixture containing RNA and DNA, which is characterized in that the method comprises steps of adsorbing and desorbing the nucleic acid in the nucleic acid mixture which contains RNA and DNA to and from a solid phase of an organic macromolecule.

The term "nucleic acid" in the invention may be a single strand or double strand, and has no limitation of a molecular weight.

The nucleic acid mixture used in the present invention means a mixture containing RNA and DNA. The type of the nucleic acid in the nucleic acid mixture may not be limited, so long as DNA and RNA are contained therein. The number of the types of the nucleic acids contained in the mixture is not also limited. The lengths of individual nucleic acids are also not particularly limited, and nucleic acids having any length ranging from several bp's to several Mbp's can be used. In view of handling, the length of nucleic acids is generally from several bp's to several hundred kbp's.

As the organic macromolecule which is used as a solid phase, acetyl cellulose is preferable. Acetyl cellulose may be any one of monoacetyl cellulose, diacetyl cellulose and triacetyl cellulose. Particularly, triacetyl cellulose is preferable. In the present invention, surface-saponified acetyl cellulose may be used as the solid phase, but acetyl cellulose which is not surface-saponified is preferably used. When surface-saponified acetyl cellulose is used, it is preferred that the surface saponification rate is lower. Specifically, an acetylcellulose having a surface-saponification rate of 0 to 50%, and more preferably an acetylcellulose having a surface-saponification rate of 0 to 20%, can be used.

As shown in the Examples below, it has been found that both of RNA and DNA are recovered by using an acetylcellulose having a high surface-saponification rate (100% of surface-saponification rate in the Example), while only RNA can be selectively recovered by using an acetylcellulose having a low surface-saponification rate (0% of surface-saponification rate in the Example). The present invention provides a method for recovering RNA selectively from a mixture containing RNA and DNA by utilizing this property.

The surface saponification means that only surface to which a saponifying agent (e.g., NaOH) contacts, is saponified. In the present invention, it is preferable that a structural body of the solid phase is kept as acetyl cellulose and only the surface of the solid phase is saponified. In this way, an amount of hydroxyl groups (density) on the surface of the solid phase can be controlled according to degree of surface saponification treatment (surface saponification degree).

In order to increase surface area of the organic macromolecule, it is preferable to form the organic macromolecule into a membrane. Further, acetyl cellulose may be a porous membrane or a non-porous membrane. However, the porous membrane is more preferable.

For example, the membrane of triacetyl cellulose is marketed as a commercial name TAC base from Fuji Photo Film K.K. As the porous membrane of triacetyl cellulose, there is Microfilter FM45 (Fuji Photo Film K.K.).

In addition, for example, it is also preferable to form the triacetyl cellulose membrane on the surface of polyethylene-made beads. In this case, triacetyl cellulose is coated on the beads. Material of the beads may be any material which does not contaminate nucleic acids, and is not limited to polyethylene.

In the present invention, RNA can be selectively separated and purified from a mixture of nucleic acids by using a solid phase of the organic macromolecule as mentioned above, preferably a solid phase of acetyl cellulose, more preferably a solid phase of triacetyl cellulose, for example, Microfilter FM45 (Fuji Photo Film K.K.) as the solid phase, and adsorbing and desorbing the nucleic acid in a nucleic acid mixture containing RNA and DNA to and from said solid phase. It has not yet been reported and has been first found by the present inventors that RNA can be selectively separated and purified by using a solid phase of the organic macromolecule as mentioned above.

In the method for separating and purifying a nucleic acid according to the present invention, adsorption and desorption of the nucleic acid can be preferably conducted by using an unit for separation and purification of nucleic acid in which a container having at least two openings contains the solid phase of the organic macromolecule.

Further preferably, adsorption and desorption of the nucleic acid can be conducted by using an unit for separation and purification of nucleic acid comprising (a) a solid phase of an organic macromolecule, (b) a container having at least two openings and containing the solid phase, and (c) a pressure difference-generating apparatus connected to one opening of the container.

In this case, a first embodiment of the method for separating and purifying a nucleic acid according to the invention can comprise the following steps of:

(a) preparing a sample solution containing a nucleic acid by using a test sample and inserting one opening of an unit for separation and purification of nucleic acid into said sample solution containing the nucleic acid;

(b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase of the organic macromolecule;

(c) making the inside of the container in a pressurized condition by using the pressure difference-generating apparatus connected to the other opening of the unit for separation and purification of nucleic acid, and discharging the sample solution containing the sucked nucleic acid to an outside of the container;

(d) inserting one opening of the unit for separation and purification of nucleic acid into the nucleic acid-washing buffer;

(e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase of the organic macromolecule;

(f) making the inside of the container in the pressurized condition by using the pressure difference-generating apparatus connected to the other opening of the unit for separation and purification of nucleic acid, and discharging the sucked nucleic acid-washing buffer to the outside of the container;

(g) inserting one opening of the unit for separation and purification of nucleic acid into the liquid capable of desorbing the nucleic acid adsorbed to the solid phase of the organic macromolecule;

(h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule to contact the liquid to the solid phase; and (i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule to the outside of the container.

A second embodiment of the method for separating and purifying a nucleic acid according to the invention can comprise the following steps of:

(a) preparing a sample solution containing the nucleic acid using a test sample and injecting said sample solution containing the nucleic acid into one opening of the unit for separation and purification of nucleic acid;

(b) making the inside of the container in the pressurized condition by using the pressure difference-generating apparatus connected to said one opening of the unit for separation and purification of nucleic acid, and discharging the injected sample solution containing the nucleic acid from the other opening to contact the sample solution to the solid phase of the organic macromolecule;

(c) injecting the nucleic acid-washing buffer into said one opening of the unit for separation and purification of nucleic acid;

(d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule;

(e) injecting the liquid capable of desorbing the nucleic acid adsorbed to the solid phase of the organic macromolecule into said one opening of the unit for separation and purification of nucleic acid; and (f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule and discharge the nucleic acid to the outside of the container.

The method for separating and purifying a nucleic acid by using the organic macromolecule will be described in detail below. Preferably in the present invention, the nucleic acid in the sample solution is adsorbed to the solid phase by contacting the sample solution containing the nucleic acid to the solid phase of the organic macromolecule, and then the nucleic acid adsorbed to the solid phase is desorbed from the solid phase by using a suitable solution described below. More preferably, the sample solution containing the nucleic acid is a solution which is obtained by adding a water-soluble organic solvent to a solution obtained by treating a cell- or virus-containing test sample with a solution capable of solubilizing a cell membrane and a nuclear membrane to disperse the nucleic acid into the solution.

The sample solution containing the nucleic acid which can be used in the present invention is not limited, but for example, in diagnostic fields, the subject solutions are the body fluid such as whole blood, serum, plasma, urine, stool, sperm and saliva which were collected as a test sample, or solutions prepared from biological materials such as plant (or a portion thereof) and animal (or a portion thereof), or their dissolved matters and homogenates.

First, these test samples are treated with an aqueous solution containing a reagent capably of lysing the cell membrane and solubilizing the nucleic acid. By this treatment, the cell membrane and the nuclear membrane are lysed, and the nucleic acid is dispersed into the aqueous solution.

For lysing the cell membrane and solubilizing the nucleic acid, for example, when the subject sample is whole blood, necessary steps are (1) removing erythrocytes, (2) removing various proteins, and (3) lysing leukocytes and lysing the nuclear membrane. (1) Removing erythrocytes and (2) removing various proteins are required to prevent non-specific adsorption to the solid phase and clogging of the porous membrane, and (3) lysing leukocytes and lysing the nuclear membrane is required to solubilize the nucleic acid which is an object of extraction. Particularly, (3) lysing leukocytes and lysing the nuclear membrane is an important step. In the method of the present invention, it is necessary to solubilize the nucleic acid in this step. For example, by incubating the sample for 10 minutes at 60° C. under the condition in which guanidine hydrochloride, Triton X100, and protease K (Sigma made) are added, the above-mentioned (1), (2) and (3) can be achieved simultaneously.

The reagent for solubilizing the nucleic acid which is used in the present invention is exemplified by the solution containing the guanidine salt, a surfactant and a protease.

The guanidine salt is preferably guanidine hydrochloride, but other guanidine salts (guanidine isothiocyanate and guanidine thiocyanate) can also be used. The concentration of guanidine salts in the solution is 0.5 M to 6 M, preferably 1 M to 5 M.

As the surfactant, Triton X100 can be used. Alternatively, an anionic surfactant such as SDS, sodium cholate and sodium sarcosinate, a nonionic surfactant such as Tween 20 and Megafac, and other various types of amphoteric surfactants, can also be used. In the present invention, the nonionic surfactant such as polyoxyethylene octylphenyl ether (Triton X100) is preferably used. The concentration of the surfactant in the solution is normally 0.05% by weight to 10% by weight, particularly preferably 0.1% by weight to 5% by weight.

As the protease, Protease K can be used, but other proteases can also give same effect. The protease is an enzyme and thus, incubation is preferable. The protease is preferably used at 37° C. to 70° C., particularly preferably at 50° C. to 65° C.

An aqueous organic solvent is added to the aqueous solution in which the nucleic acid is dispersed, to contact the nucleic acid to the organic macromolecule. By this operation, the nucleic acid in the sample solution is adsorbed to the organic macromolecule. In order to adsorb the nucleic acid which was solubilized by the operation as described hereinabove to the solid phase of the organic macromolecule, it is necessary that an aqueous organic solvent is mixed with the solubilized nucleic acid mixture solution, and a salt is present in the obtained nucleic acid mixture solution.

By breaking a hydrating structure of a water molecule present around the nucleic acid, the nucleic acid is solubilized in an unstable state. It is presumed that when the nucleic acid in such state is contacted to the solid phase of the organic macromolecule having a hydroxyl group on the surface, a polar group on the surface of the nucleic acid interacts to the polar group on the surface of the solid phase and the nucleic acid is adsorbed to the surface of the solid phase. In the method of the present invention, the state of the nucleic acid can become unstable by mixing the aqueous organic solvent with the solubilized nucleic acid mixture solution and by the presence of the salt in the obtained mixture solution of the nucleic acid.

Sugar moiety of DNA is deoxyribose, while that of RNA is ribose. Therefore, RNA has one more hydroxyl group per base as compared with DNA, and thus interaction between RNA and a polar group on the surface of the solid phase tends to occur. By utilizing the intensity of this interaction, RNA is separated and purified from a mixture of nucleic acids containing RNA and DNA.

The aqueous organic solvent used herein is exemplified by ethanol, isopropanol or propanol. Among them, ethanol is preferable. The concentration of the aqueous organic solvent is preferably 5% by weight to 90% by weight, and more preferably 20% by weight to 60% by weight. It is particularly preferable to make the concentration of ethanol to be added as high as possible in a degree in which no coagulant occurs.

As the salt present in the obtained mixture solution of the nucleic acid, various chaotropic substances (guanidium salt, sodium iodide, and sodium perchlorate), sodium chloride, potassium chloride, ammonium chloride, sodium bromide, potassium bromide, calcium bromide, ammonium bromide and the like are preferable. Particularly, guanidium salt has both effects of lysis of cell membrane and solubilization of the nucleic acid, and therefore is particularly preferable.

Subsequently, the organic macromolecule to which the nucleic acid is adsorbed, is contacted to the nucleic acid-washing buffer solution. This buffer solution has a function of washing out impurities in the sample solution which are adsorbed to the organic macromolecule together with the nucleic acid. Consequently, the solution should have a composition having no ability of desorbing the nucleic acid from the organic macromolecule and an ability of desorbing the impurities. The nucleic acid-washing buffer solution is an aqueous solution comprising a main agent, a buffer agent and when required, a surfactant. The main agent is exemplified by an about 10 to 100% by weight (preferably about 20 to 100% by weight and more preferably about 40 to 80% by weight) aqueous solution of methanol, ethanol, isopropanol, n-propanol, butanol, acetone and the like. The buffer agent and the surfactant are exemplified by the previously described buffer agents and surfactants. Among them, a solution containing ethanol, Tris and Triton X100 is preferable. The preferable concentrations of Tris and Triton X100 are 10 to 100 mM and 0.1 to 10% by weight, respectively.

Then, to the solution capable of desorbing the nucleic acid adsorbed to the organic macromolecule, is contacted the washed organic macromolecule as described above. This solution contains the target nucleic acid and hence, is collected and subjected to amplification of the nucleic acid by following operation, e.g., PCR (polymerase chain reaction) It is preferable that the solution capable of desorbing the nucleic acid has a low salt concentration and particularly preferably, the solution of 0.5 M or lower salt concentration is used. For this solution, purified distilled water, TE buffer and the like can be used.

The unit for separation and purification of nucleic acid which is used in the invention is an unit for separation and purification of nucleic acid wherein the solid phase of the organic macromolecule is contained in the container having at least two openings.

The material of the container is not particularly limited, so long as the organic macromolecule is contained therein and at least two openings can be provided. In view of easiness of manufacturing, a plastic is preferable. For example, clear or opaque resins such as polystyrene, polymethacrylate ester, polyethylene, polypropylene, polyester, nylon, or polycarbonate are preferably used.

FIG. 1 shows a conceptual diagram of the container. Basically, the container has a section for containing the solid phase, and the solid phase is contained said containing section. The solid phase does not move out of the containing section at the time of sucking and discharging the sample solution and the like. A pressure difference-generating apparatus, e.g., a syringe, is connected to the opening. For this purpose, it is preferable that the container is initially divided into two sections, and after the solid phase is contained, these portions are integrated. In addition, in order to prevent that the solid phase moves out of the containing section, a mesh made of the material which does not contaminate DNA, can be placed on the top and the bottom of the solid phase.

There is no limitation on the shape of the organic macromolecule which is contained in the container as described above. The shape may be any shape such as discoid, squared, rectangular or ellipsoid; and in the membrane, cylindrical, roll, or beads coated with the organic macromolecule having a hydroxyl group on the surface. In view of manufacturing suitability, the shape having symmetric property such as discoid, squared, cylindrical and roll, and beads are preferable.

The one opening of the container described above is inserted into the sample solution containing the nucleic acid, and the sample solution is contacted to the organic macromolecule by sucking from the other opening. The sample solution is discharged, and then the nucleic acid-washing buffer solution is sucked and discharged. Then, the solution capable of desorbing the nucleic acid adsorbed to the organic macromolecule is sucked and discharged. This discharged solution is collected to obtain the target nucleic acid.

Alternatively, by dipping the organic macromolecule in the sample solution containing the nucleic acid, the nucleic acid-washing buffer solution, and the solution capable of desorbing the nucleic acid adsorbed to the organic macromolecule, in this order, the target nucleic acid can be obtained.

The unit for separation and purification of nucleic acid used in the invention preferably comprises (a) a solid phase of the organic macromolecule, (b) a container containing the solid phase and having at least two openings, and (c) a pressure difference-generating apparatus connected to one opening of the container. The unit for separation and purification of nucleic acid will be described below.

The container is normally made in a divided form of a main body which contains the solid phase of the organic macromolecule, and a lid, wherein each has at least one opening. The one is used as an inlet and an outlet of the sample solution containing the nucleic acid, the nucleic acid-washing buffer solution, a liquid capable of desorbing the nucleic acid adsorbed to the solid phase (hereinafter referred to as "sample solution and the like"); and the other is connected to the pressure difference-generating apparatus capable of making the inside of the container in a reduced pressure or pressurized state. There is no limitation of the shape of the main body. In order to make manufacture easy and also make entire diffusion of the sample solution on the solid phase easy, it is preferable that the section is a circular shape. In order to prevent a cutting wastage of the solid, it is also preferable that the section is a squared shape.

It is necessary to connect the lid to the main body so as to make the inside of the container in the reduced pressure state or the pressurized state by using the pressure difference-generating apparatus. If this state is accomplished, the method of connection can be selected freely. For example, use of an adhesive, screwing, fitting, securing, and fusing by ultrasonic heating, are exemplified.

An internal volume of the container is determined only by an amount of the sample solution to be treated. Normally, it is expressed by the volume of the solid phase to be contained. It is preferable to use a size suitable for containing 1 to 6 sheets of the solid phase having about 1 mm or smaller (e.g. around 50 to 500 μm) thickness and about 2 mm to 20 mm diameter.

It is preferable to make an end of the solid phase to contact closely to an inner wall face of the container to prevent the sample solution and the like from being passed.

The bottom surface of the solid phase that is located oppositely to the opening used as the inlet of the sample solution and the like, is not closely contacted to the inner wall of the container, and a space is provided. Thereby, a structure suitable for achieving diffusion of the sample solution and the like evenly as possible on the entire surface of the solid phase, can be formed.

It is preferable to provide a member having a hole in generally a center thereof on the solid phase located oppositely to the other opening, i.e., the opening connected to the pressure difference-generating apparatus. This member pushes the solid phase, and has an efficient effect of discharging the sample solution and the like. This member has preferably a shape having a slope such as a funnel or a cup in such a way that the liquid is collected in the center hole. The size of this hole, an angle of the slope, and the thickness of the member can be properly determined by those skilled in the art in consideration of the amount of the sample solution and the like to be treated and the size of the container for containing the solid phase. Between this member and the opening, a space is preferably provided to store the overflowed sample solution and the like and prevent the sample solution from being sucked into the pressure difference-generating apparatus. The volume of this hole can be properly chosen by those skilled in the art. In order to collect efficiently the nucleic acid, it is preferable to suck the sample solution containing the nucleic acid in an amount which is sufficient for dipping a whole of the solid phase.

In order to prevent the sample solution and the like from being concentrated only beneath the opening through which sucking is carried out and to allow the sample solution and the like to be passed through the solid phase, a space is preferably provided between the solid phase and this member. For this purpose, it is preferable to provide a plurality of projection from the member to the solid phase. The size and number of the projection can be properly chosen by those skilled in the art. It is preferable to make an opening area of the solid phase as large as possible while keeping the space.

When the container has 3 or more openings, in order to make possible sucking and discharging the liquid by pressure-reducing and pressuring operations, it is needless to say that an excess opening should be closed temporarily.

The pressure difference-generating apparatus reduces at first the pressure of the inside of the container which contains the solid phase, so as to suck the sample solution containing the nucleic acid. The pressure difference-generating apparatus is exemplified by the syringe, pipetter, or a pump capable of sucking and pressurizing such as a peristaltic pump. Among them, the syringe is suitable for manual operation and the pump is suitable for automatic operation. The pipetter has an advantage of one hand operation. Preferably, the pressure difference-generating apparatus is releasably connected to the one opening of the container.

Next, the purification method of the nucleic acid using the unit for separation and purification of nucleic acid as described above, will be described. First of all, in the sample solution containing the nucleic acid is inserted one opening of the unit for separation and purification of nucleic acid as described above. Then, by using the pressure difference-generating apparatus connected to the other opening, the pressure of the inside of the purifying unit is reduced to suck the sample solution into the container. By this operation, the sample solution is contacted to the solid phase so as to adsorb the nucleic acid present in the sample solution to the solid phase. At this time, it is preferable to suck the sample solution in such an amount that the solution can be contacted to almost whole of the solid phase. However, sucking of the solution in the pressure difference-generating apparatus causes contamination of the apparatus and hence, the amount is appropriately adjusted.

After an appropriate amount of the sample solution is sucked, the inside of the container of the unit is pressurized by using the pressure difference-generating apparatus, and the sucked liquid is discharged. No interval is required for this operation, and discharge may be carried out immediately after sucking.

Subsequently, the nucleic acid-washing buffer solution is sucked into the container and discharged from it by pressure-reducing and pressurizing operations as described above to wash the inside of the container. This solution has functions of washing out the sample solution left in the container and also washing out impurities in the sample solution adsorbed to the solid phase together with the nucleic acid. Therefore, the solution must have a composition having functions of desorbing no nucleic acid but impurities from the solid phase. The nucleic acid-washing buffer solution is an aqueous solution containing a main agent, a buffer agent and when required, a surfactant. The main agent is exemplified by about 10 to 90% (preferably about 50 to 90%) aqueous solution of methyl alcohol, ethyl alcohol, butyl alcohol, acetone and the like; and the buffer agent and the surfactant are exemplified by the previously described buffer agents and surfactants. Among them, a solution containing ethyl alcohol, Tris and Triton X100 is preferable. The preferable concentrations of Tris and Triton X100 are 10 to 100 mM and 0.1 to 10%, respectively.

Next, a solution capable of desorbing the nucleic acid adsorbed to the solid phase is introduced into the inside of the container and discharged from the container by pressure-reducing and pressurizing operations as described above. This discharged solution contains the target nucleic acid and hence, the target nucleic acid can be collected to be subjected to amplification of the nucleic acid by a following operation, e.g., PCR (polymerase chain reaction).

Figure 2:
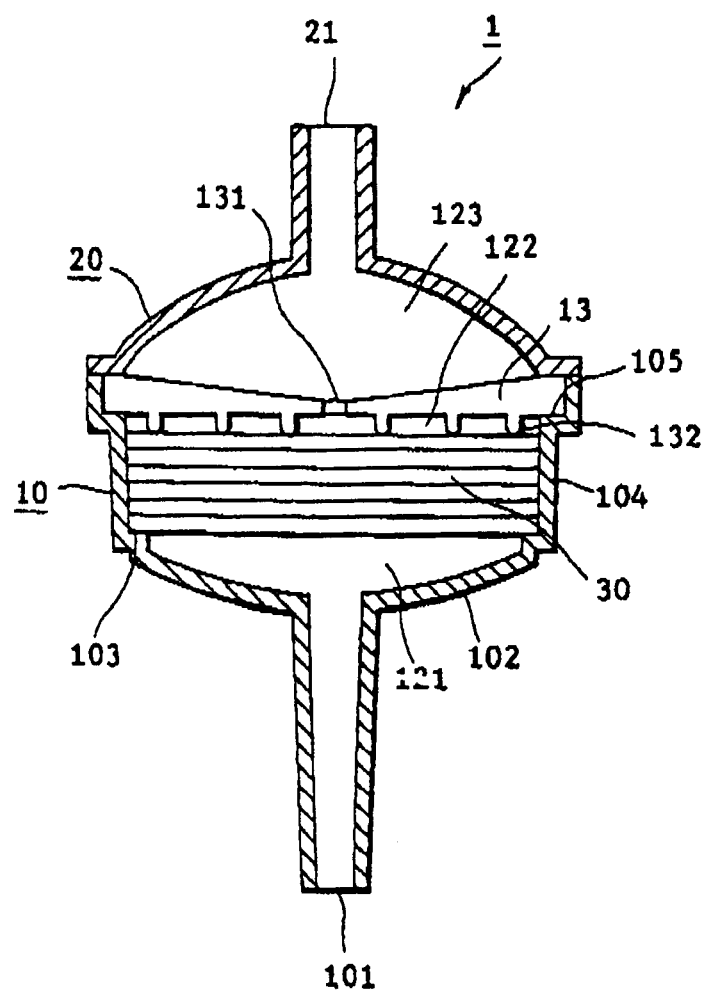
FIG. 2 is an example of the unit for separation and purification of nucleic acid according to the present invention, wherein the pressure difference-generating apparatus to be connected to the opening 21 is not illustrated.

FIG. 2 is a sectional view of an example of the unit for separation and purification of nucleic acid according to the present invention, provided that no pressure difference-generating apparatus is illustrated. A container 1 containing the solid phase comprises a main body 10 and a lid 20 and is made of clear polystyrene. The main body 10 contains saponified triacetyl cellulose membrane as a solid phase 30. In addition, it has an opening 101 for sucking the sample solution and the like. A bottom face 102 extending from the opening is formed in a funnel shape, and a space 121 is formed between this and the solid phase 30. In order to support the solid phase 30 and hold the space 121, a frame 103 which is formed with the bottom face 102, is provided.

The main body has an inner diameter of 20.1 mm, a depth of 5.9 mm, and a length from the bottom face 102 to the opening 101 of about 70 mm. The solid phase 30 which is contained has a diameter of 20.0 mm. The thickness of one sheet of the solid phase is about 50 to 500 μm, and an example of the thickness is 100 μm.

In FIG. 2, a funnel-shaped pressing member 13 is provided on the top of the solid phase. A hole 131 is made in a center of the pressing member 13, and a group of projections 132 are provided downward, and a space 122 is formed between this and the solid phase 30. To prevent leaking of the sample solution and the like from a space between the solid phase 30 and a wall 104 of the main body 10, the inner diameter of the upper portion of the wall 104 is larger than the diameter of the solid phase. The periphery of the pressing member 13 is mounted on a step 105.

A lid 20 is connected to the main body 10 by ultrasonic heating. In almost central part of the lid 20 is provided an opening 21 for connecting the pressure difference-generating apparatus. Between the lid 20 and the pressing member 13 is provided a space 123 for holding the sample solution and the like which flow out from the hole 131. A volume of the space 123 is about 0.1 mL.

The present invention will be described in more detail with reference to examples. However, the present invention is not limited to these examples.

EXAMPLES

Example 1

(1) Preparation of Cartridge for Purification of Nucleic Acid

Figure 3:
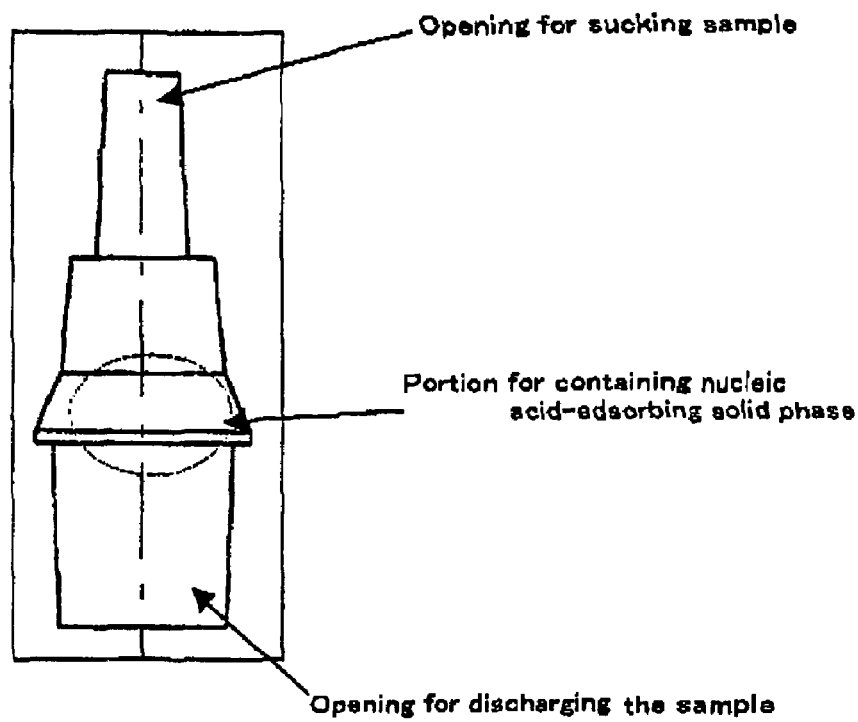
FIG. 3 is a schematic diagram of a cartridge for purification of nucleic acid used in the Example.

A cartridge for purification of nucleic acid having a portion which has 7 mm inner diameter and 2 mm thickness for containing a solid phase for adsorption of a nucleic acid, was prepared by high impact polystyrene. FIG. 3 shows a structure of the prepared cartridge for purification of nucleic acid. This cartridge for purification of nucleic acid has an opening for sucking a sample, a portion for containing a nucleic acid-adsorbing solid phase, and an opening for discharging the sample. A suction pump is connected to the opening for discharging the sample to suck the sample.

(2) Preparation of Solid Phase for Purification of Nucleic Acid

Fuji Microfilter FM45 (Fuji Photo Film K.K.) was used as a solid phase for adsorbing nucleic acid. This solid phase is composed of triacetyl cellulose (not saponified). As a comparative solid phase, Fuji Microfilter FR25 (Fuji Photo Film K.K.; triacetyl cellulose having a pore size of 2.5 μm and a surface saponification rate of 100%). These solid phases were contained in the portion for containing a nucleic acid-adsorbing solid phase, of the cartridge for purification of nucleic acid which was prepared in the above (1).

(3) Preparation of Adsorption Buffer Solution and Washing Buffer Solution for Purification of Nucleic Acid An adsorption buffer solution and a washing buffer solution for purification of nucleic acid, the compositions of which are shown in Table 1, were prepared.

TABLE 1

| [adsorption buffer] | |
|---|---|
| Guanidine hydrochloride (Life Technology made) | 382 g |
| Tris (Life Technology made) | 12.1 g |
| Triton X100 (ICN made) | 10 g |
| Distilled water | 1000 mL |
| [washing buffer] | |
| 10 mM Tris-HCl 65% ethanol | |

(4) Operation of Nucleic Acid Purification

An aqueous solution containing 1.3 kbp DNA (50 ng/μL) and an aqueous solution containing human total RNA (50 ng/μL) were prepared. To 200 μL of each of the aqueous DNA solutions were added 200 μL of the adsorption buffer and 200 μL of ethanol, and the mixture was stirred. After stirring, each liquid was sucked and discharged by using cartridges for purification of the nucleic acid having the solid phase for purification of nucleic acid which were prepared in the above (1) and (2).

Moreover, impurities on the cartridge and the adsorbing solid phase were washed out by sucking and discharging 500 μL of the washing buffer.

Finally, 200 μL of distilled water was sucked to collect this liquid.

(5) Quantification of the Amount of Collected Nucleic Acid

By measuring, an optical absorption of each of the collected liquid at 260 nm, an amount of the collected DNAs was quantified. The results are shown in Table 2 and FIG. 4. The result of agarose gel electrophoresis using the collected liquid is shown in FIG. 5.

TABLE 2

| | no. | | | | | | | | |
|---|---|---|---|---|---|---|---|---|---|
| | 230 | 260 | 280 | 320 | 260/280 | factor | ng/μl | vol. (μl) | (μg) |
| Total RNA | | | | | | | | | |
| Comparative | 0.485 | 0.893 | 0.413 | 0.004 | 2.1741 | 40 | 89 | 100 | 8.9 |
| Present Invention | 0.405 | 0.667 | 0.314 | 0.009 | 2.157 | 40 | 66 | 100 | 6.6 |
| 1.3 Kbp DNA | | | | | | | | | |
| Comparative | 0.425 | 0.908 | 0.476 | 0.000 | 1.908 | 50 | 91 | 100 | 9.1 |
| Present Invention | 0.222 | 0.029 | 0.013 | 0.000 | 2.231 | 50 | 3 | 100 | 0.3 |

Figure 4:
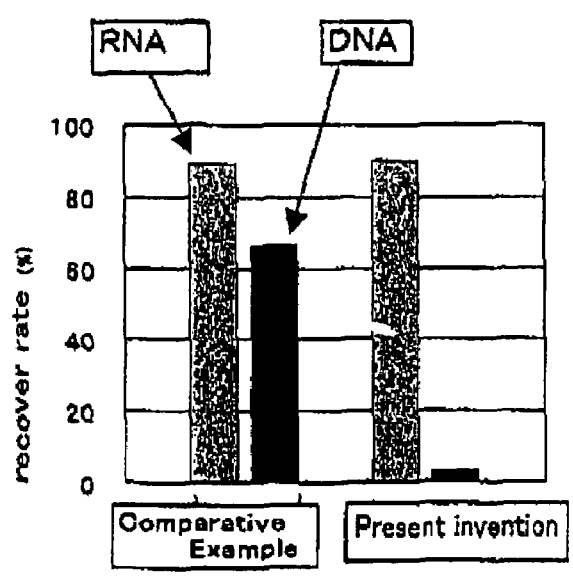
FIG. 4 shows the result of measurement of a collection rate of the nucleic acid which was separated and purified according to the method of the present invention.
Figure 5:
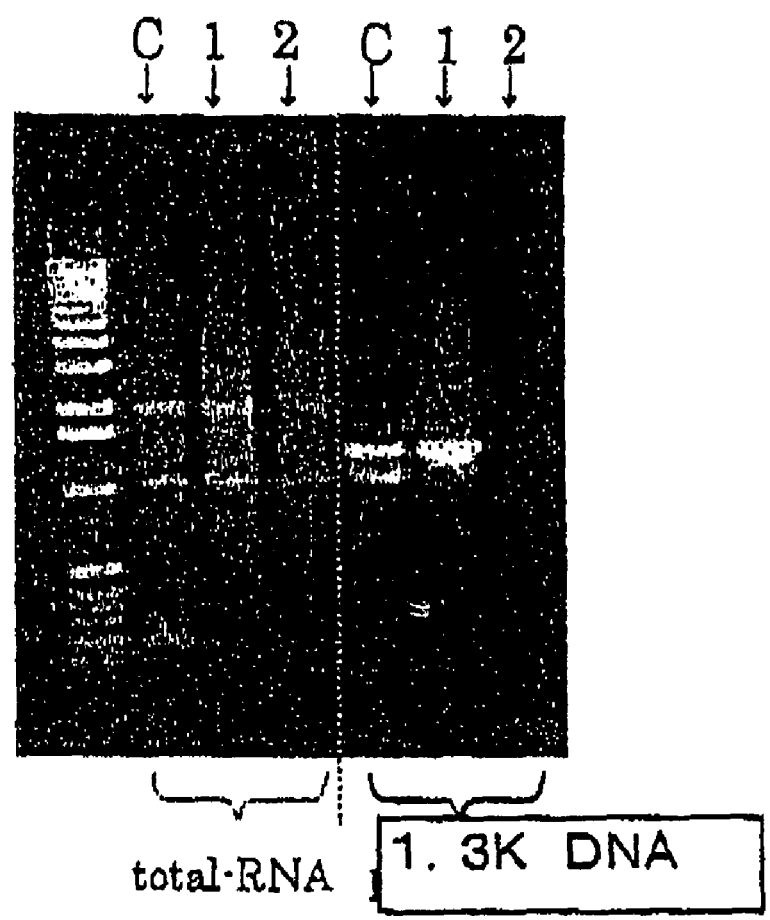
FIG. 5 shows the result of electrophoresis of the nucleic acid which was separated and purified from a mixture of nucleic acids according to the method of the present invention.

As is understood from the results of Table 2 and FIGS. 4 and 5, it has been found that RNA can be selectively recovered by allowing the nucleic acid to be adsorbed to the solid phase of an organic macromolecule according to the present invention.

INDUSTRIAL APPLICABILITY

By the method for separating and purifying a nucleic acid according to the present invention, which uses a solid phase which is excellent in separation performance, good in washing efficiency, easy in processing, and is capable of mass-production of those having substantially same separation performance, RNA can be separated and purified from the nucleic acid mixture containing RNA and DNA. In addition, operations become easy by using the unit for separation and purification of nucleic acid which was described in the present specification.

What is claimed is:

1. A method for separating and purifying RNA from a nucleic acid mixture, comprising a step of:
   adsorbing and desorbing a nucleic acid in the nucleic acid mixture containing RNA and DNA to and from a solid phase of an organic macromolecule,
   wherein the organic macromolecule is an acetylcellulose having a surface-saponification rate of 0 to 50%.

2. The method according to claim 1, wherein the organic macromolecule is an acetylcellulose having a surface-saponification rate of 0 to 20%.

3. The method according to claim 1, wherein acetylcellulose is a porous film.

4. The method according to claim 1, wherein acetylcellulose is a non-porous film.

5. The method according to claim 1, wherein acetylcellulose is coated on beads.

6. The method according to claim 1, wherein the nucleic acid in a sample solution is adsorbed to and desorbed from the solid phase of organic macromolecule.

7. The method according to claim 6, wherein the sample solution is a solution prepared by adding a water-soluble organic solvent to a solution obtained by treating a cell- or virus-containing test sample with a nucleic acid-solubilizing reagent.

8. The method according to claim 7, wherein the nucleic acid-solubilizing reagent is a guanidine salt, a surfactant and a proteolytic enzyme.

9. The method according to claim 1, comprising steps of:
   adsorbing the nucleic acid to the solid phase of the organic macromolecule; washing the solid phase using a nucleic acid-washing buffer; and
   desorbing the nucleic acid adsorbed to the solid phase by using a liquid capable of desorbing the nucleic acid adsorbed to the solid phase.

10. The method according to claim 9, wherein the nucleic acid-washing buffer is a solution containing 20 to 100% by weight of methanol, ethanol, isopropanol or n-propanol.

11. The method according to claim 9, wherein the liquid capable of desorbing the nucleic acid adsorbed to the solid phase is a solution having a salt concentration of 0.5 M or lower.

12. The method according to claim 1, wherein adsorption and desorption of the nucleic acid is carried out by using an unit for separation and purification of nucleic acid in which a container having at least two openings contains the solid phase of the organic macromolecule.

13. The method according to claim 1, wherein adsorption and desorption of the nucleic acid is carried out by using an unit for separation and purification of nucleic acid which comprises
   (a) a solid phase of the organic macromolecule,
   (b) a container having at least two openings and containing the solid phase, and
   (c) a pressure difference-generating apparatus connected to one opening of the container.

14. The method according to claim 13, comprising steps of:
   (a) preparing a sample solution containing a nucleic acid by using a test sample and inserting one opening of an unit for separation and purification of nucleic acid into said sample solution containing the nucleic acid;
   (b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase of the organic macromolecule;
   (c) making the inside of the container in a pressurized condition by using the pressure difference-generating apparatus connected to the other opening of the unit for separation and purification of nucleic acid, and discharging the sample solution containing the sucked nucleic acid to an outside of the container;
   (d) inserting one opening of the unit for separation and purification of nucleic acid into a nucleic acid-washing buffer;
   (e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase of the organic macromolecule;
   (f) making the inside of the container in the pressurized condition by using the pressure difference-generating apparatus connected to the other opening of the unit for separation and purification of nucleic acid, and discharging the sucked nucleic acid-washing buffer to the outside of the container;
   (g) inserting one opening of the unit for separation and purification of nucleic acid into a liquid capable of desorbing the nucleic acid adsorbed to the solid phase of the organic macromolecule;
   (h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule to contact the liquid to the solid phase; and (i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule to the outside of the container.

15. The method according to claim 13, comprising steps of:
   (a) preparing a sample solution containing the nucleic acid using a test sample and injecting said sample solution containing the nucleic acid into one opening of the unit for separation and purification of nucleic acid;
   (b) making the inside of the container in the pressurized condition by using the pressure difference-generating apparatus connected to said one opening of the unit for separation and purification of nucleic acid, and discharging the injected sample solution containing the nucleic acid from the other opening to contact the sample solution to the solid phase of the organic macromolecule;
   (c) injecting a nucleic acid-washing buffer into said one opening of the unit for separation and purification of nucleic acid;
   (d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule;
   (e) injecting a liquid capable of desorbing the nucleic acid adsorbed to the solid phase of the organic macromolecule into said one opening of the unit for separation and purification of nucleic acid; and
   (f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule and discharge the nucleic acid to the outside of the container.

* * * * *